United States Patent
Walsh et al.

(10) Patent No.: US 10,416,089 B1
(45) Date of Patent: Sep. 17, 2019

(54) SYSTEM AND METHOD FOR VALIDATING CLEANLINESS OF A SURFACE

(71) Applicant: Center for Pharmaceutical Cleaning Innovation Corp., Hillsborough, NJ (US)

(72) Inventors: Andrew Walsh, Somerville, NJ (US); Xi Wang, West Lebanon, NH (US); Nick Downey, Catonsville, MD (US)

(73) Assignee: CENTER FOR PHARMACEUTICAL CLEANING INNOVATION CORP, Hillsborough, NJ (US)

( * ) Notice: Subject to any disclaimer, the term of this patent is extended or adjusted under 35 U.S.C. 154(b) by 10 days.

(21) Appl. No.: 15/647,452

(22) Filed: Jul. 12, 2017

Related U.S. Application Data

(60) Provisional application No. 62/361,272, filed on Jul. 12, 2016.

(51) Int. Cl.
```
G06K 9/00      (2006.01)
G01N 21/94     (2006.01)
G06T 7/00      (2017.01)
G06T 7/33      (2017.01)
```
(52) U.S. Cl.
CPC ............ *G01N 21/94* (2013.01); *G06T 7/001* (2013.01); *G06T 7/337* (2017.01)

(58) Field of Classification Search
CPC ............ B01D 46/0004; B01D 2279/65; B01D 46/2411; B01D 46/0091; D06F 43/02; D06F 35/006; G01N 21/94; G06T 7/337
See application file for complete search history.

(56) References Cited

U.S. PATENT DOCUMENTS

| | | | | |
|---|---|---|---|---|
| 5,397,683 A | * | 3/1995 | Roland | G03F 7/2022 430/292 |
| 2007/0254825 A1 | * | 11/2007 | Shannon | A61K 8/0208 510/441 |
| 2010/0200019 A1 | * | 8/2010 | Prioli | B08B 9/08 134/22.1 |
| 2015/0184332 A1 | * | 7/2015 | Cuppini | D06F 43/02 8/142 |
| 2016/0069743 A1 | * | 3/2016 | McQuilkin | G01J 3/2803 356/416 |
| 2018/0280852 A1 | * | 10/2018 | Jehle | B01D 46/0004 |

\* cited by examiner

*Primary Examiner* — Amir Alavi
(74) *Attorney, Agent, or Firm* — Myers Wolin, LLC

(57) ABSTRACT

This disclosure describes a system and method for documenting and/or quantifying the inspection of the cleanliness of a surface. The documenting is attained through the capture of an image of the surface and uploading said image along with metadata about the image to a place of secure storage such as a company internal server or a web server. The quantification is attained through image analysis of the image, with or without enhancements such as UV light, to derive a value for the amount of residue remaining on the surface. This quantification can be performed on a device and sent to a server, or performed on the server itself after the image has been sent. In all cases, the inspection of cleanliness is documented with or without quantification.

12 Claims, 9 Drawing Sheets

Red:

Green:

Blue:

SYSTEM AND METHOD FOR VALIDATING CLEANLINESS OF A SURFACE

CROSS-REFERENCE TO RELATED APPLICATIONS

This application claims the benefit of U.S. Provisional Patent Application No. 62/361,272, filed Jul. 12, 2016, the contents of which are incorporated by reference herein.

FIELD OF THE INVENTION

The present invention is in the technical field of evaluating the cleanliness of a surface. More particularly, the present invention is in the technical field of visual inspection of a potentially contaminated surface.

BACKGROUND

In many industries, including the pharmaceutical, biotech and medical device industries, manufacturing and device surfaces must be cleaned after use to remove potentially harmful contaminants. The sufficient cleaning of such surfaces is often critical and must be performed prior to resuming use of the surfaces for a new process. For example, in the pharmaceutical industry, if machinery is used to process a first product, it must be sufficiently cleaned before transitioning to use of the same machine for a second product so as to avoid cross contamination of the second product with the first product.

In order to insure the effectiveness of a cleaning process, the process applied to such surfaces must be verified to have been effective prior to releasing the surface for use on a new process or product. For example, federal regulations require inspection of manufacturing surfaces prior to returning those surfaces to use.

Inspection is typically performed through visual inspection by human operators. However, visual inspection is prone to variation and errors due to differences in lighting conditions, viewing angle and distance, eyesight and age of inspector, training of the operator, or lack thereof, and a wide variety of other variables. Further, visual inspection has not been qualified as a method. If an inspector approves a surface after inspection, the actual level of residue on the surface is not known at the time of inspection as the inspection process is not validated as to its accuracy, precision, or linearity or limits of detection. Further, there is no documentation that the visual inspection was actually performed other than by the signature of the operator.

Previous approaches to these problems typically relate to providing training to inspectors to better observe and evaluate residues on surfaces. This may be through training inspectors using "coupons" standards illustrating residue levels. However, none of these previous approaches have been demonstrated to be consistently accurate, precise, linear, or what their limits of detection are and they do not generate documented evidence that the visual inspection was actually performed.

Further, these previous approaches do not provide quantification of the residue amount. Although a visual "threshold" limit may be assumed from published literature, no calculated value or assumed value is provided by the inspection. Accordingly, existing processes are qualitative (Pass/Fail) and subjective instead of quantitative and objective, and therefore are not consistent and repeatable.

SUMMARY

Described herein are systems and methods for conducting real-time analysis of trace residues of compounds remaining on surfaces after cleaning through image processing and analysis of images captured as part of the process. Such images may be captured using, for example, a smartphone camera. An application implementing the method can create calibration curves using photos of known quantities of residue of compounds placed on surrogate surfaces, such as coupons, and may then compare the images captured to the calibration curve, yielding accurate, precise and linear quantification of the residue amounts.

An application implementing the method can store several linearity calibration curves for different compounds prior to practical testing operations, and during operation, a user may then select a provided calibration curve corresponding to the compound he/she wants to analyze. Alternatively, a general calibration curve may be selected that is not compound-specific.

After analysis using a calibration curve, the application implementing the method may automatically upload the results of the analysis onto a server with a date and time stamp as well as an identification of the user performing the analysis, as well as other metadata, to ensure data integrity.

In some embodiments, the capturing of images may be aided with a UV light, and the method may then amplify the residue signal up to 10 times and reach a lower limit of detection than the human eye.

DETAILED DESCRIPTION OF THE PREFERRED EMBODIMENTS

Figure 1A:
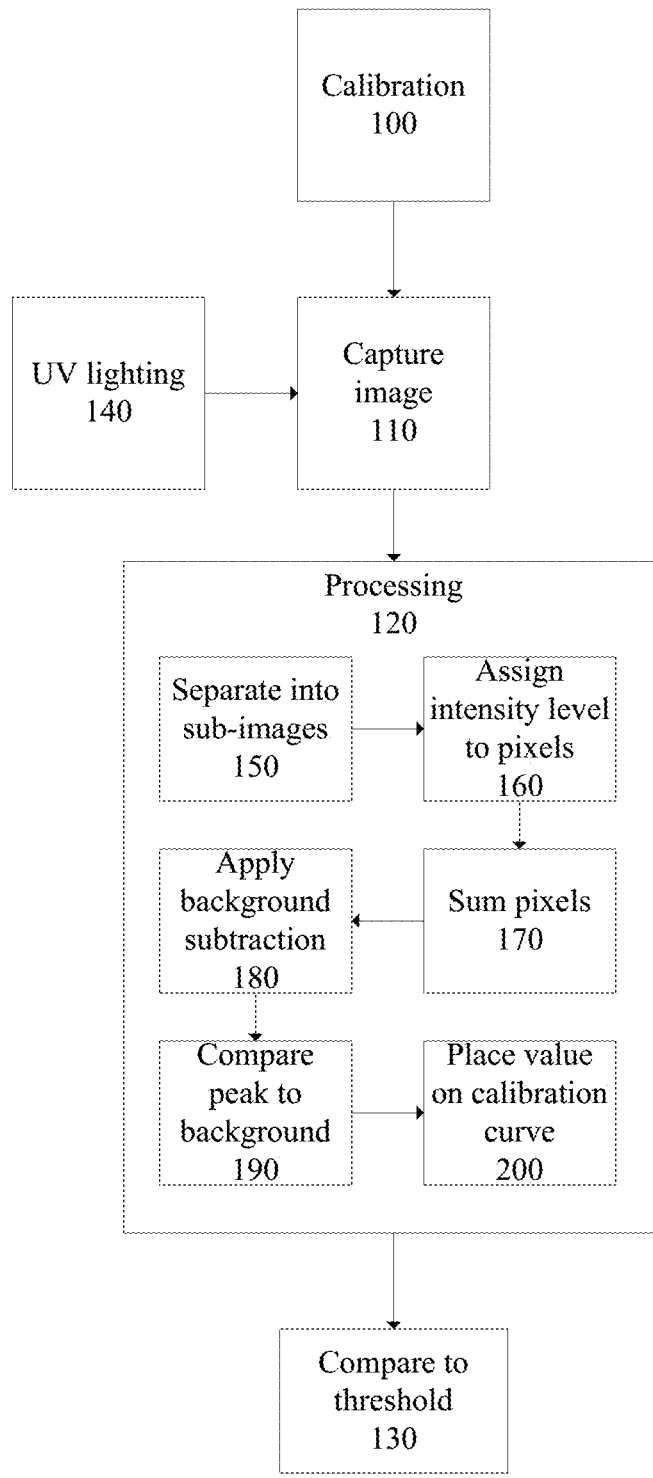
FIG. 1A is a flowchart illustrating a method for confirming the cleanliness of a surface.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom"

as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

Figure 10:
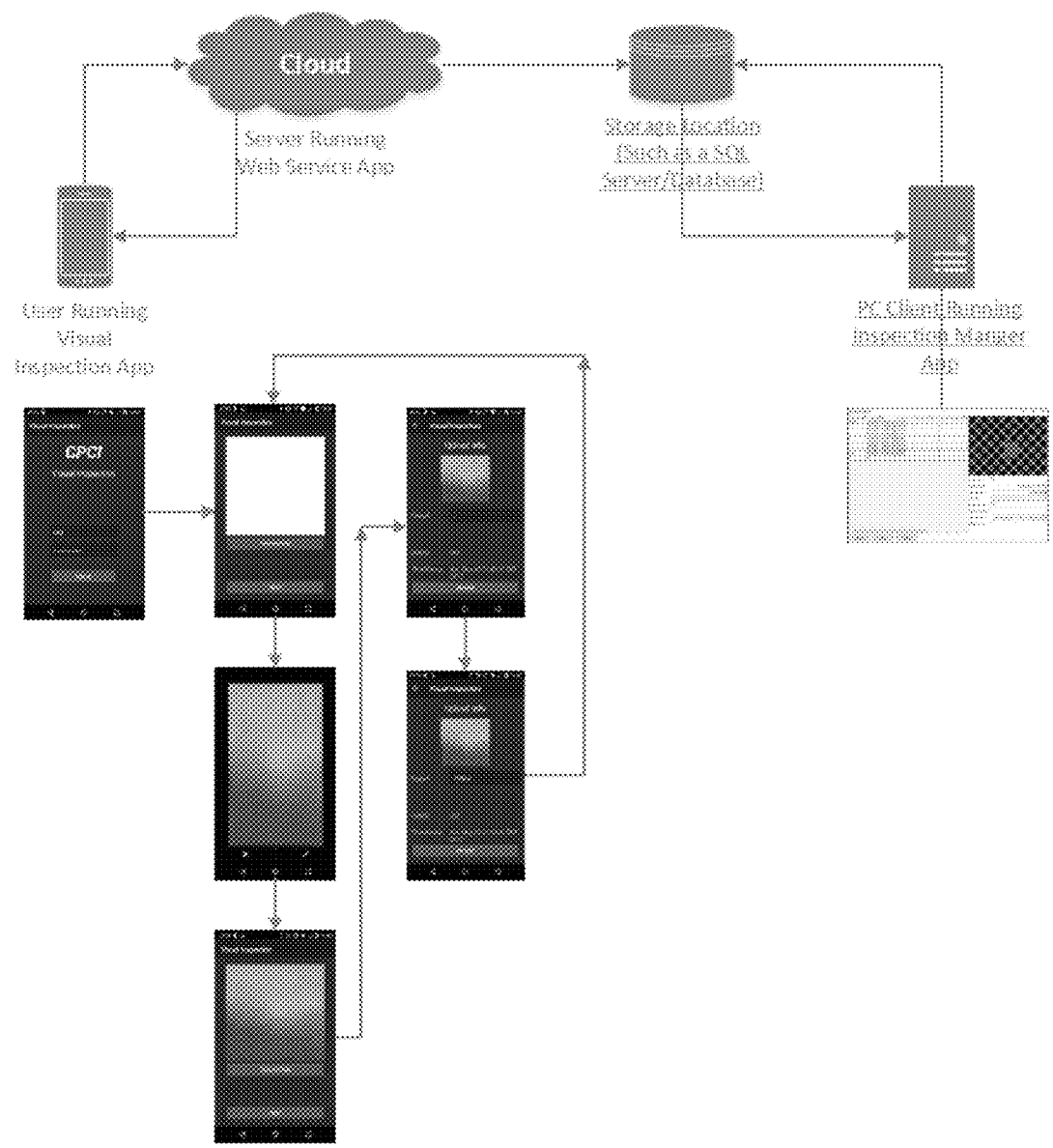
FIG. 10 is a schematic diagram of a system for implementing the method of FIG. 1.
Figure 11:
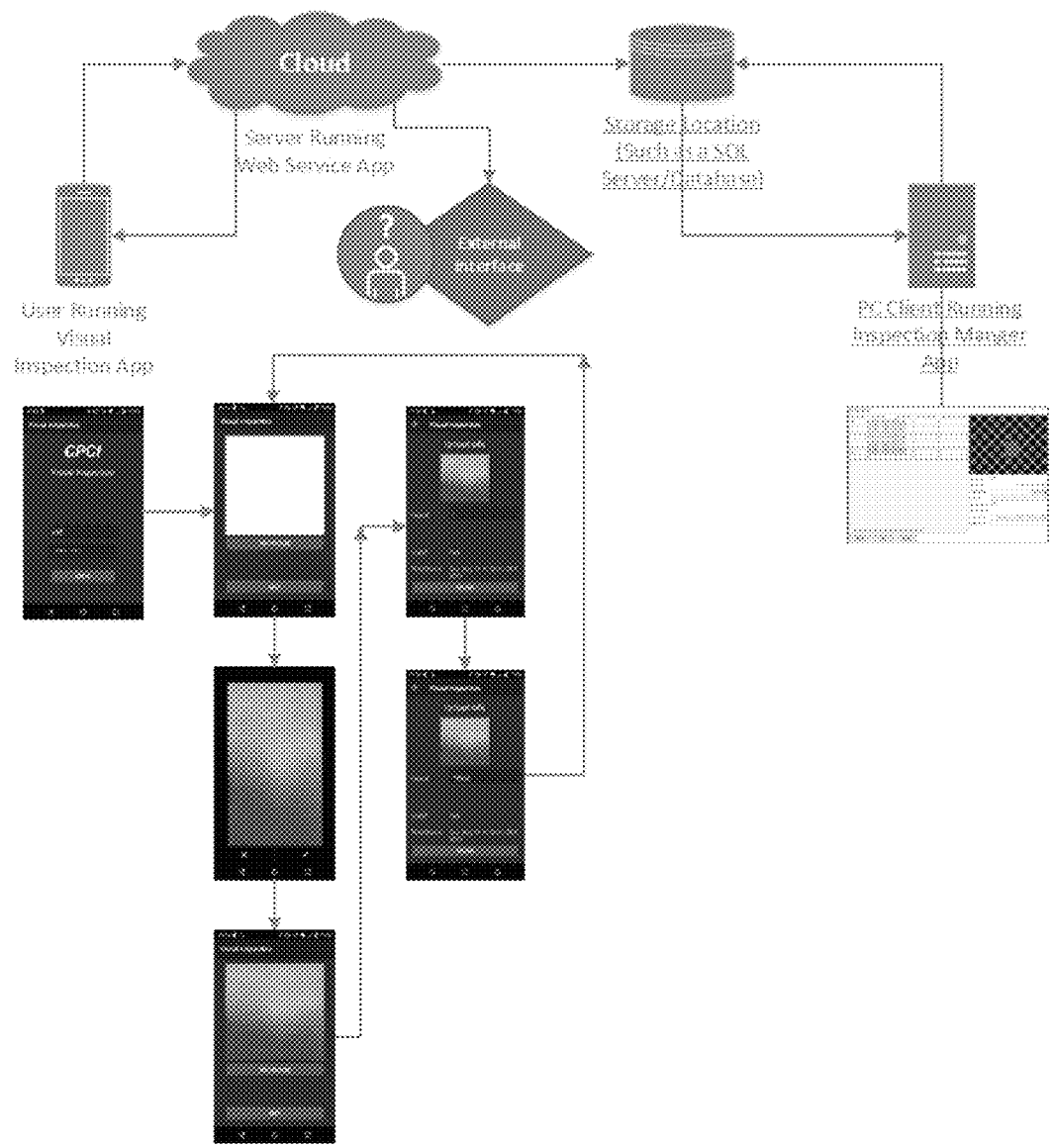
FIG. 11 is a schematic diagram of another system for implementing the method of FIG. 1.

A system and method are provided for confirming the cleanliness of a surface. Typically, after machinery, a product or other equipment is used for a manufacturing process, the method will be applied prior to releasing the machinery for use in a different manufacturing process. The method may be implemented in the form of an application for use on a smartphone. Accordingly, parts of the method may be described in relation to smartphone components. Alternative implementations are considered as well. For example, portions of the method may be implemented on a smartphone and portions may be performed on a server that receives data from the smartphone. The method may similarly be implemented in other hardware forms, as well as in custom hardware devices designed for implementing the methods described. A device for implementing the method is described below in relation to FIG. 9. Systems for implementing the method are shown in FIGS. 10 and 11.

FIG. 1A is a flowchart illustrating a method for confirming the cleanliness of a surface. Initially, the method will be calibrated (100) in light of the particular contaminant or surface type. The calibration process will be described in more detail below, but typically, a user will either select a stored calibration curve corresponding to the contaminant, or group of contaminants, being evaluated or will choose to create a new calibration curve.

Figure 3:
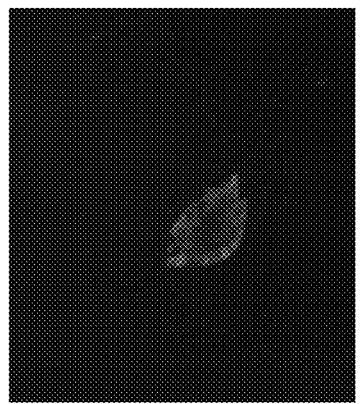
FIG. 3 is a sample image captured in the method of FIG. 1.

After calibration, an image of the surface is captured (110). This may be by, for example, using a smartphone camera. An example of such a captured image is shown in FIG. 3. The captured image is then processed (120) to determine a quantity of contaminant on the surface being evaluated. The result of the image processing (at 120) is then compared to an expected result to determine if the quantity of contaminant is less than a threshold amount (130). If the quantity of contaminant is less than the threshold amount, the surface and associated equipment may be confirmed as clean and may, for example, be released for use in manufacturing process.

In some embodiments, the image is captured (at 110) using a camera with an ultraviolet (UV) light (140). This may enhance the contrast of a contaminant with a background surface. For example, most substances, or mixtures, when illuminated with UV, will fluoresce in a certain color, usually green or blue. The surface being evaluated is typically made from a material less likely to fluoresce. Stainless steel, for example, refracts little or no UV light, and will therefore show up as a darker surface.

Accordingly, even if a substance does not have any fluorescent qualities, the use of a UV light will still cause the background to remain dark and therefore may still act as a good light for the images.

Figure 4A:
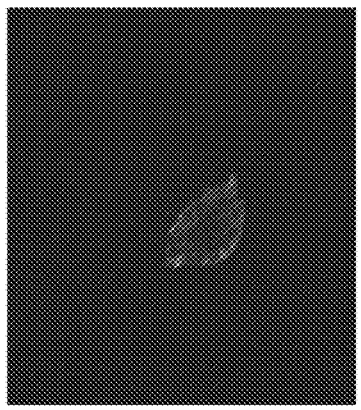
FIGS. 4A, 4B and 4C are three sub-images extracted from the image of FIG. 1.
Figure 4B:
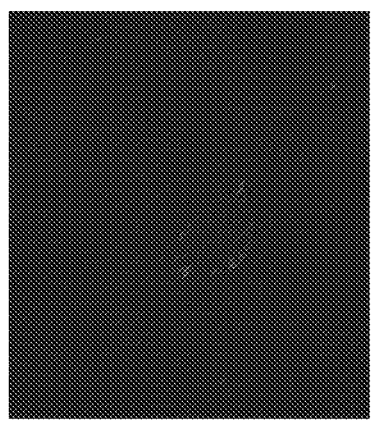
Figure 4C:
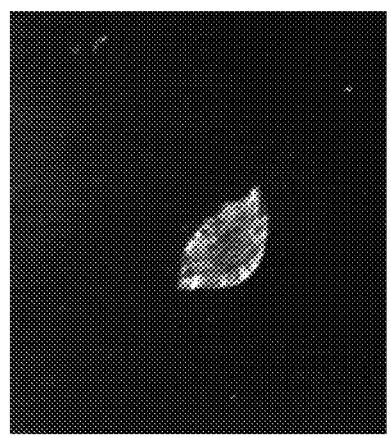

The image processing (performed at 120) may be implemented in several ways to determine a quantity of contaminant. One such implementation is shown in the flowchart. A captured image may be separated into component sub-images (150), each containing a different color component of the captured image. For example, an additive color model, such as an RGB model, may be used. As such, the image may be separated into red, green, and blue sub-images, as shown in FIGS. 4A-C, each of which may then be processed separately.

Figure 5A:
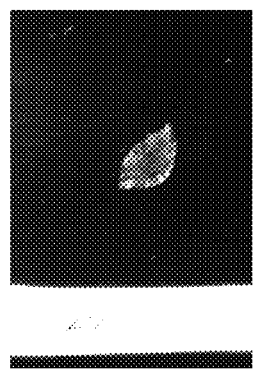
FIG. 5A is a sample sub-image to be processed.

Accordingly, the processing of the sub-images is described with respect to the blue sub-image, as shown in FIG. 5A, but is repeated for each component sub-image extracted. The sub-images comprise pixels, and each pixel of the blue sub-image is assigned an intensity level (160). The intensity level may be normalized, and as such, each pixel may be given a value between 0 and 1. Prior to evaluating the intensity levels, the sub-image may be converted to grayscale in order to ease processing.

Figure 5B:
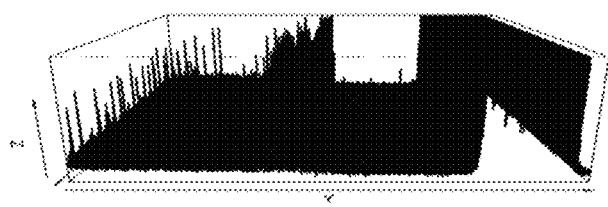
FIG. 5B is a 3D plot of image intensities of the image of FIG. 5A.
Figure 6:
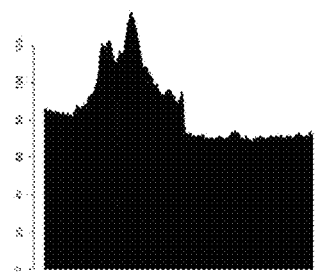
FIG. 6 is a 2D plot illustrating a portion of the 3D plot of FIG. 5B.

The blue sub-image may then be assigned a coordinate plane including an X and Y axis, and the pixels may then be broken up into rows, so that each point along the Y axis has a row of pixels extending in the direction of the X axis. This may be visualized using a 3D map as shown in FIG. 5B. Each row of pixels may then be summed along the X axis (170) and combined into an array for processing. The results of this summation is shown in the 2D plot of FIG. 6.

Figure 7:
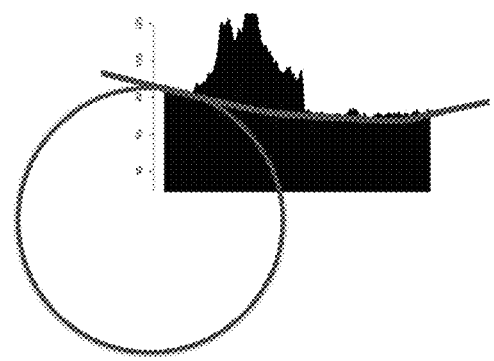
FIG. 7 is an illustration of a peak subtraction method applied to the 2D plot of FIG. 6.

A rolling-ball background subtraction process may then be implemented (180). Such a process isolates peaks in a data set from background noise, and is illustrated in FIG. 7. In this case, the background noise is the intensity of the color content of the blue sub-image in the background section of the image while the peak values are the intensities associated with the actual contaminant.

Rolling ball background subtraction processes are typically applied directly to images. However, in this case, the method applies the rolling ball methodology to an array of summations, rather than directly to the image, in order to gather additional information of lower-end residue amounts. In other embodiments, a different method may be used to determine background levels, or other implementations of a rolling ball method may be used, so long as lower-end residue amounts are still captured.

The peak values extracted from the data set are then compared to the background values (190) to determine a residue amount for the blue sub-image. This comparison may be by, for example, calculating the residue volume (Rv) by dividing the area of the peak (Mp) by the mean of the background (Mb). Other calculations are contemplated as well, such as calculations to normalize the values based on how much surface area is captured.

The process similarly extracts a residue volume for each of the remaining sub-images, and selects the largest value and places it on the calibration curve (200) to determine if the value is less than the threshold amount (at 130). For example, a calibration curve, generated using the process described below with respect to FIG. 1B, will generally be a straight line of the form y=kx+b, where x is the image intensity extracted from the images and y is the resulting residue amount. Accordingly, the image analysis applies the curve to the detected image intensity, and compares the resulting residue amount to a threshold amount. In some embodiments, the calibration curve may be able to provide a theoretical threshold image intensity derived from the curve, such that the image intensity detected may be compared to a threshold image intensity level.

Alternatively a separate camera may be used to capture an image and transmit the image to a processing device for processing.

Using the method described, in one implementation, the limit of detection is 4.5 ug/9 cm$^2$, or 0.5 ug/cm$^2$, which is approximately 8 times better than a human's limit of detection, which is approximately 4 ug/cm$^2$. Furthermore, this approach provides quantification not available with a human observer. A wide range of contaminant levels allows for good linearity (such as r$^2$=0.95) in the evaluation of the surface.

Figure 1B:
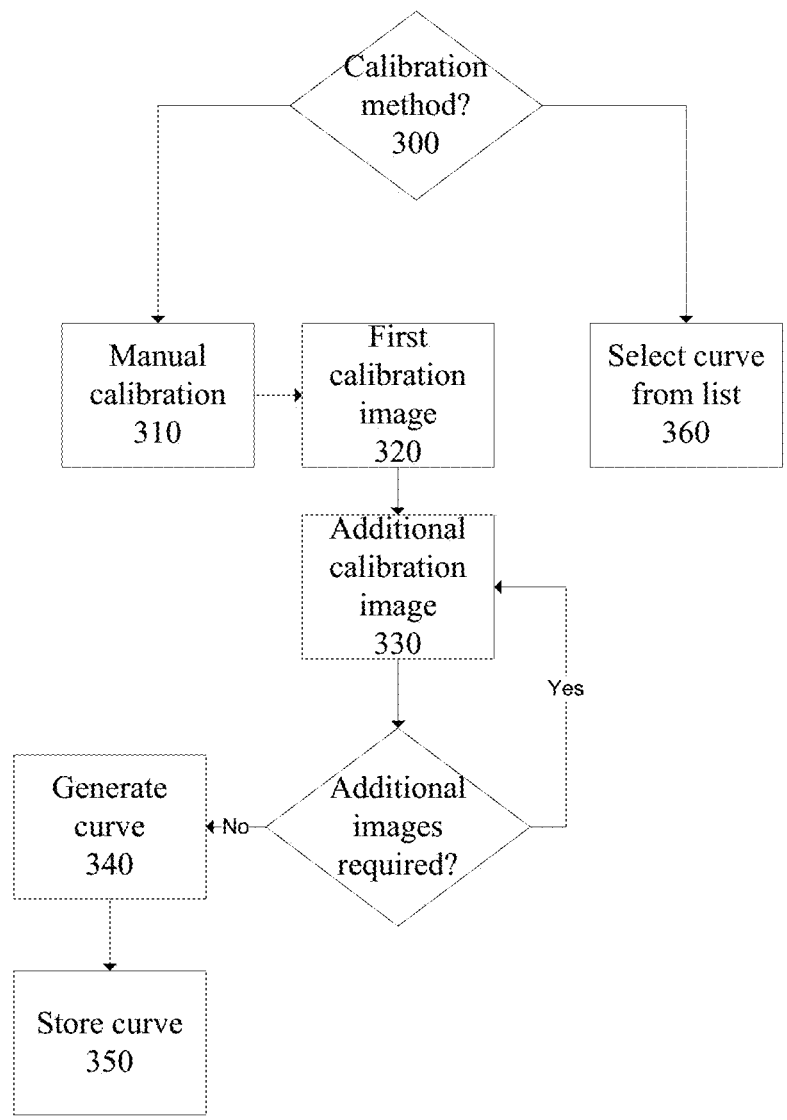
FIG. 1B is a flowchart illustrating a calibration process for use in the method of FIG. 1.

FIG. 1B is a flowchart illustrating a calibration process for use in the method of FIG. 1. Upon initiating an implementation of the method, a user may choose whether to calibrate the method based on a stored curve or based on manual calibration (300).

If the user chooses to manually calibrate (310), they may capture a first calibration image of a surface having a known amount of contaminant (320) and a second calibration image of a similar surface having a different known amount of contaminant (330). The calibration method may then generate a curve (340) based on those two known levels of contaminant, and a user may be able to evaluate an unknown amount of contaminant using that curve. In some cases, two calibration images may be sufficient, but if the calibration method requires additional data to generate the calibration curve, additional images may be required. Calibration images are typically taken of coupons containing known amounts of contaminants.

After generating the calibration curve, a user may store the curve 350 and associate it with a specific type of contaminant such that it may be used in future instances of evaluating the same contaminant. A user may further store the curve to a centralized database so that other users may use the stored calibration curve as well.

Instead of manually calibrating, a user may choose to select a previously saved calibration curve 360. In such a case, a user may select a calibration curve associated with the type of contaminant being evaluated. This may include curves generated previously by himself or by others using the manual calibration process (at 310).

The curves generated may then be used in processing images (at 120) in the method shown in FIG. 1B.

Figure 2:
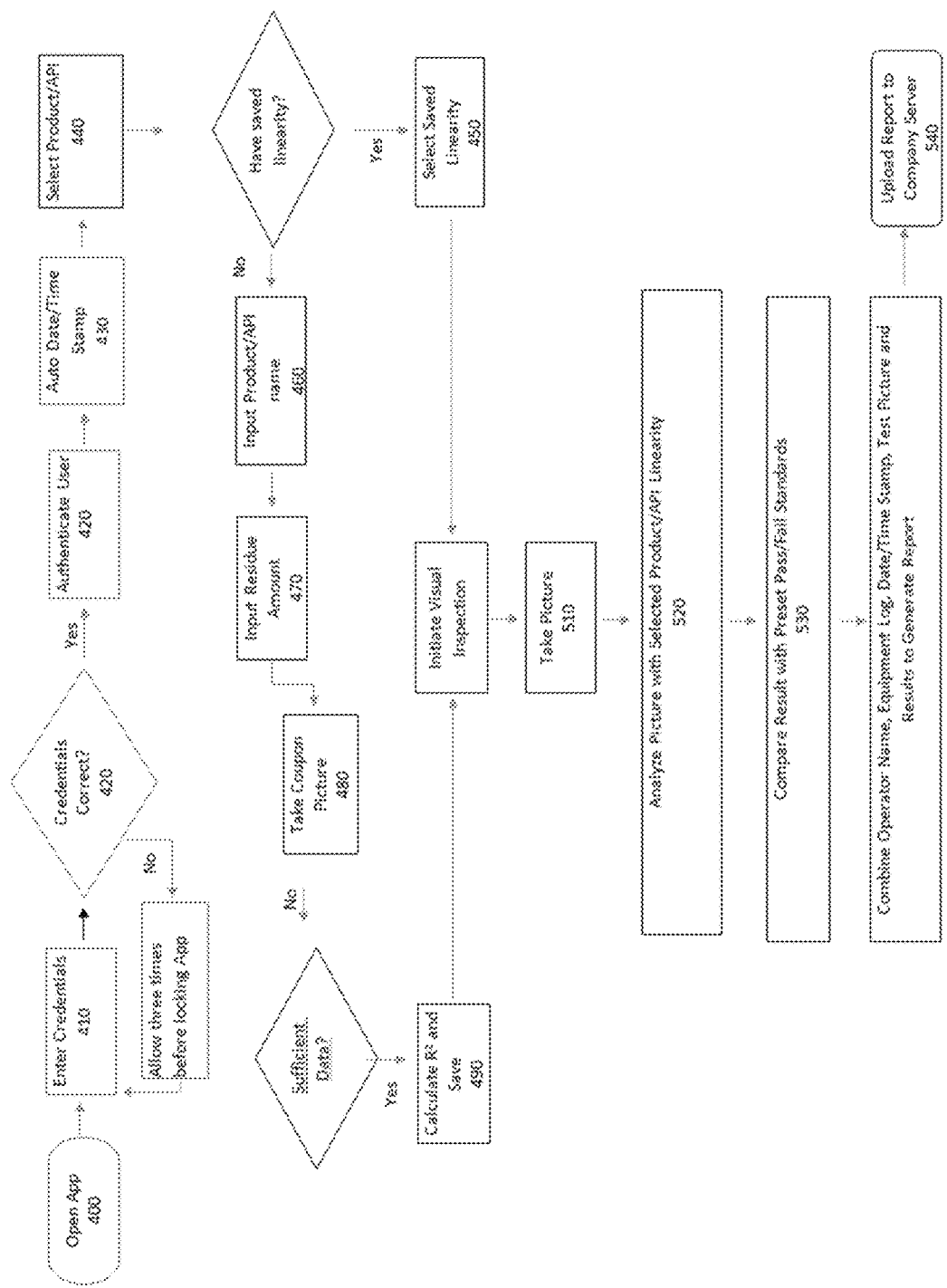
FIG. 2 is a flowchart illustrating an application implementing the method of FIG. 1.

FIG. 2 is a flowchart illustrating an application, such as a smartphone application, implementing the method of FIG. 1. Such an application may conduct a real-time analysis of trace residues of compounds remaining on surfaces through image processing and analysis of photos taken using the cell phone camera by implementing the methods described above. Such an application may therefore create calibration curves using photos of standard residues of compounds on surrogate surfaces, and the calibration curves may then be used to compare photos of unknown residues yielding accurate and precise linear quantification of the residue amount.

As shown, a user may open an application (400) and enter credentials (410). After confirming that the credentials are correct, a user may enter user information (420) which may trigger an automatic date and time stamp (430) associated with the user's session.

The user may then apply the calibration method shown in FIG. 1B by selecting a product (440) to be evaluated. If there is a saved calibration curve, or linearity, associated with the product selected, a user may select it (450). Otherwise, the user may input a new product name (460), input a known residue or contaminant amount (470) and capture a calibration image (480). The application may require a user to repeat the process until sufficient data can be generated based on the calibration images. Once sufficient data is available, a calibration curve is calculated and saved (490) in relation to the newly identified product.

The application then allows a user to begin testing (500) by capturing an image (510), analyzing the image (520), and comparing the results to a threshold (530) as discussed with respect to FIG. 1A. Finally, the application will then combine operator, equipment log, date and time stamps, the test picture, and the test results into a report that is then uploaded to a company server (540). Alternatively, the application may send the metadata and the test picture which will then be subsequently analyzed on the server to derive the test results. In a simplified employment of the application, the application may only send the test picture along with any metadata to the server for storage only, with no analysis, as simple documentation that the inspection took place.

Figure 8A:
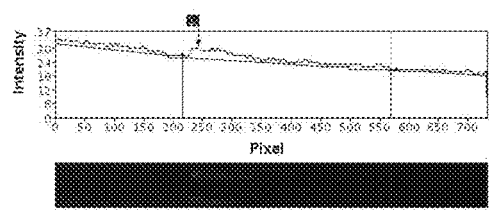
FIGS. 8A and 8B illustrate the amplification of a signal by using UV light.
Figure 8B:
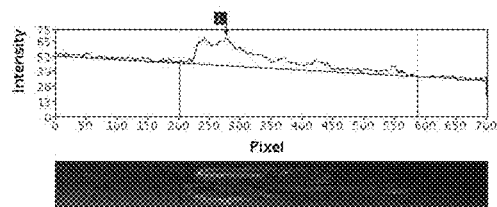

FIGS. 8A-B illustrate the amplification of a signal by using UV light, with FIG. 8A illustrating a resulting intensity curve before applying UV light, and FIG. 8B illustrating a resulting intensity curve after applying UV light.

Figure 9:
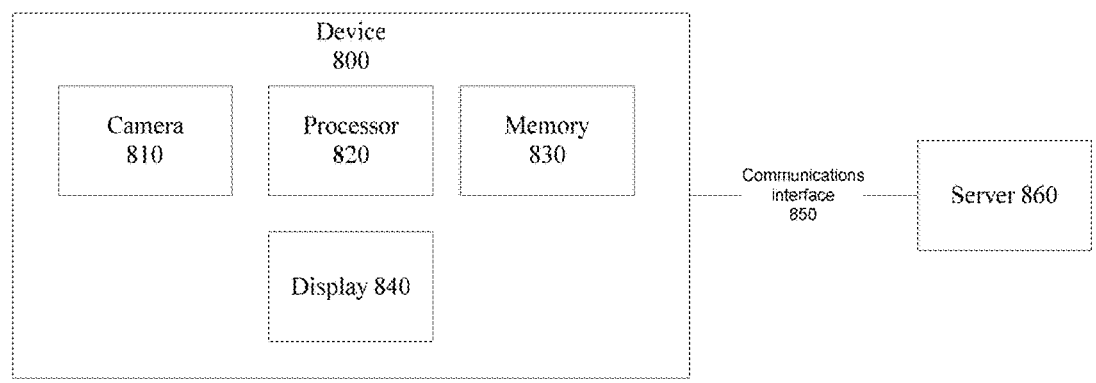
FIG. 9 is a schematic diagram of a device for implementing the method of FIG. 1.

FIG. 9 is a schematic diagram of a device 800 for implementing the method of FIG. 1, shown as part of a system. Such a device 800 may be, for example, a smartphone containing application software, and typically contains a camera 810, a processor 820, and a memory 830, as well as a display 840 for implementing a user interface. Accordingly, the memory 830 may store instructions for implementing the method outlined in FIGS. 1A-2, and the processor 820 may execute the instructions using the camera 810 to capture images and the display 840 to provide results to a user. Alternatively, instructions for implementing the method may be stored on a server with the method executed on the server.

The device 800 may further contain a communication interface 850 for communicating with a server 860. Accordingly, the device 800 may utilize the communication interface 850 to retrieve stored calibration curves or other data and upload the results of the evaluation process implemented to the server 860. Example system implementations of the above method are shown in FIGS. 10 and 11.

In some embodiments the systems and methods described herein may be used as a means of quality control for a process, such as an equipment cleaning process for equipment used in a manufacturing process. Similarly, the systems and methods may be used as part of an equipment inventory management process or supply chain management process. In such embodiments, a piece of equipment passing through an inventory management process may be used for a first manufacturing process and cleaned in preparation for a second cleaning process. The system and method described may then be applied to the piece of equipment, and the equipment may be allowed to advance to the next step of the inventory management process only if cleanliness is confirmed by the process.

Accordingly, in some embodiments, after a piece of equipment is used for a first manufacturing process, an inventory management platform may apply a "cleaning hold" or the like. Such a cleaning hold would not allow the equipment to be used for a second process until the hold is released. One way to remove the cleaning hold would then be to apply the system and method of the present disclosure to the equipment, and once cleanliness is confirmed, the equipment would be released. For example, the system and method may interface with other manufacturing software such as SAP, MES, TrackWise, etc. to release the equipment back into manufacturing or to allow the release of product for further processing.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" and like terms encompass all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A method for confirming the cleanliness of a surface, the method comprising:
    capturing an image of a surface;
    processing the captured image to determine a quantity of a contaminant on the surface, the quantity being determined as a mass per surface area; and
    outputting confirmation of the cleanliness of the surface only if the quantity of contaminant determined is less than a predetermined threshold amount selected from several potential threshold amounts based on an identification of the contaminant as one of several potential contaminants,
    the method further comprising a calibration process comprising:
        capturing a first calibration image with a first known contamination amount, the first known contamination amount being a mass per surface area;
        capturing a second calibration image with a second known contamination amount, the second known contamination amount being a mass per surface area; and
        generating a linear curve representing projected quantities of contamination on the surface in the form of a mass per surface area,
        wherein the processing of the captured image results in determining a location on the linear curve representing the captured image.

2. The method of claim 1, further comprising illuminating the surface with a UV light while capturing the image of the surface.

3. The method of claim 1, wherein the capturing of the image is with a smartphone camera and wherein the processing of the captured image is in a smartphone application.

4. The method of claim 1, further comprising selecting one of several calibration curves, wherein each calibration curve represents a known contaminant or group of contaminants on a known surface or group of surfaces, and wherein the processing of the captured image results in determining a location on the selected calibration curve representing the captured image.

5. A method for confirming the cleanliness of a surface, the method comprising:
    capturing an image of a surface;
    processing the captured image to determine a quantity of a contaminant on the surface, the quantity being determined as a mass per surface area;
    outputting confirmation of the cleanliness of the surface only if the quantity of contaminant determined is less than a predetermined threshold amount selected from several potential threshold amounts based on an identification of the contaminant as one of several potential contaminants; and
    instructing an inventory system to release an apparatus comprising the surface upon confirming the cleanliness of the surface,
    wherein the release is based on an acceptable analysis of the test picture in a device, along with an upload of the test results with its metadata.

6. A method for confirming the cleanliness of a surface, the method comprising:
    capturing an image of a surface;

processing the captured image to determine a quantity of a contaminant on the surface, the quantity being determined as a mass per surface area;

outputting confirmation of the cleanliness of the surface only if the quantity of contaminant determined is less than a predetermined threshold amount selected from several potential threshold amounts based on an identification of the contaminant as one of several potential contaminants; and instructing an inventory system to release an apparatus comprising the surface upon confirming the cleanliness of the surface, wherein the release is based on: (a) an acceptable analysis of the test picture on a server, along with an upload of the test results with its metadata, or (b) a successful upload of an acceptable test picture with its metadata to provide a documentation that an inspection has taken place.

7. A method for confirming the cleanliness of a surface, the method comprising:

capturing an image of a surface;

processing the captured image to determine a quantity of a contaminant on the surface, the quantity being determined as a mass per surface area; and outputting confirmation of the cleanliness of the surface only if the quantity of contaminant determined is less than a predetermined threshold amount selected from several potential threshold amounts based on an identification of the contaminant as one of several potential contaminants, wherein the predetermined threshold amount is the maximum safe surface residue for the contaminant on the surface.

8. The method of claim 7, wherein the maximum safe surface residue is as referenced in ASTM E3106-18 Standard Guide for Science-Based and Risk-Based Cleaning Process Development and Validation and corresponds to a maximum safe carryover of a contaminant over a total surface area of the equipment or device the contaminant is found on.

9. A method for confirming the cleanliness of a surface, the method comprising:

capturing an image of a surface;

processing the captured image to determine a quantity of a contaminant on the surface, the quantity being determined as a mass per surface area; and outputting confirmation of the cleanliness of the surface only if the quantity of contaminant determined is less than a predetermined threshold amount for the contaminant;

wherein the processing of the captured image comprises separating the image into red, blue, and green sub-images, each of the sub-images comprising pixels;

determining a normalized intensity for each pixel in each of the sub-images; and summing the normalized intensities for pixels in each of the sub-images.

10. The method of claim 9, wherein, for each sub-image, the normalized intensities are summed along a first axis of the sub-image and the sums are arrayed along a second axis of the sub-image perpendicular to the first.

11. The method of claim 10, wherein the processing of the captured image further comprises:

determining a background intensity by applying a rolling ball algorithm across the sums arrayed along the second axis for each of the sub-images;

comparing a peak intensity to the background intensity for each sub-image; and determining a residue volume for each sub-image by dividing a summation of all pixel intensities within the peak by the average background intensity.

12. The method of claim 11, further comprising selecting the one of the sub-images demonstrating the largest mass per surface area and comparing the associated residue mass per surface area to the threshold amount.

* * * * *